United States Patent
Lockwood, Jr.

(10) Patent No.: US 8,342,173 B2
(45) Date of Patent: Jan. 1, 2013

(54) NASAL DILATOR WITH CUSHION LAYER AND VARIABLE SPRING RATE

(75) Inventor: Hanford N. Lockwood, Jr., San Mateo, CA (US)

(73) Assignee: Silver Eagle Labs Inc., Carson City, NV (US)

( * ) Notice: Subject to any disclaimer, the term of this patent is extended or adjusted under 35 U.S.C. 154(b) by 1390 days.

(21) Appl. No.: 11/880,217

(22) Filed: Jul. 19, 2007

(65) Prior Publication Data

US 2009/0020115 A1 Jan. 22, 2009

(51) Int. Cl.
*A61F 5/56* (2006.01)
*A62B 7/00* (2006.01)
*A61M 29/00* (2006.01)

(52) U.S. Cl. ............ 128/200.24; 128/848; 128/207.18; 606/199; 606/204.45

(58) Field of Classification Search ............. 128/200.24, 128/204.12, 206.18, 207.14, 207.18, 848, 128/912, DIG. 26; 606/191, 196, 199, 204.45; 602/54, 56, 58
See application file for complete search history.

(56) References Cited

U.S. PATENT DOCUMENTS

| | | | |
|---|---|---|---|
| 5,476,091 A | 12/1995 | Johnson | |
| 5,479,944 A | 1/1996 | Petruson | |
| 5,533,499 A | 7/1996 | Johnson | |
| 5,546,929 A | 8/1996 | Muchin | |
| RE35,408 E | 12/1996 | Petruson | |
| 5,611,333 A | 3/1997 | Johnson | |
| 5,653,224 A * | 8/1997 | Johnson | 128/200.24 |
| 5,706,800 A | 1/1998 | Cronk et al. | |
| 5,718,224 A | 2/1998 | Muchin | |
| 5,769,089 A | 6/1998 | Hand et al. | |
| 5,806,525 A * | 9/1998 | Pope, Jr. | 128/848 |
| 5,890,486 A * | 4/1999 | Mitra et al. | 128/200.24 |

(Continued)

FOREIGN PATENT DOCUMENTS

ES 289561 10/1985

(Continued)

OTHER PUBLICATIONS

Aso LLC drawing No. 045 QA02NASALSH, dated Jun. 3, 2004.

*Primary Examiner* — Justine Yu
*Assistant Examiner* — Valerie L Skorupa
(74) *Attorney, Agent, or Firm* — Michael Best & Friedrich LLP

(57) ABSTRACT

A nasal dilator capable of introducing separating stresses in nasal outer wall tissues has a resilient member and a pair of spaced-apart end surfaces which can be forced toward one another from an initial flat position of the dilator to thereby substantially reduce the direct spacing therebetween by an external spacing reducing force. This results in restoring forces in the dilator tending to return it to the original direct spacing between the end surfaces. Resilient members, which can be asymmetrical with respect to a centerline of the dilator that is parallel to the long axis of the dilator, have a spring rate which continuously diminishes from the centerline to the end surfaces. The edges of the resilient members are contiguous to the edge of the cushion layer so that adhesive on the cushion layer is at the same level as the bottom surface of the resilient members. An adhesive on the end surfaces adhesively engages exposed surfaces of nasal outer wall tissues sufficiently to keep the dilator attached to the nasal wall surfaces while subjecting them to the restoring forces.

40 Claims, 5 Drawing Sheets

U.S. PATENT DOCUMENTS

| | | |
|---|---|---|
| 5,913,873 A | 6/1999 | Blach et al. |
| 5,931,854 A | 8/1999 | Dillon |
| 5,957,126 A | 9/1999 | Neeser |
| 6,006,746 A | 12/1999 | Karell |
| 6,029,658 A | 2/2000 | De Voss |
| 6,058,931 A | 5/2000 | Muchin |
| 6,065,470 A | 5/2000 | Van Cromvoirt et al. |
| 6,098,616 A * | 8/2000 | Lundy et al. ............. 128/200.24 |
| 6,244,265 B1 | 6/2001 | Cronk et al. |
| 6,276,360 B1 | 8/2001 | Cronk et al. |
| 6,318,362 B1 | 11/2001 | Johnson |
| 6,375,667 B1 | 4/2002 | Ruch |
| 6,453,901 B1 * | 9/2002 | Ierulli ...................... 128/200.24 |
| 6,550,474 B1 | 4/2003 | Anderson et al. |
| 6,694,970 B2 * | 2/2004 | Spinelli et al. ........... 128/200.24 |
| 6,769,428 B2 | 8/2004 | Cronk et al. |
| 6,769,429 B1 | 8/2004 | Benetti |
| 6,823,864 B2 | 11/2004 | Blach et al. |
| 7,013,889 B2 | 3/2006 | Cronk et al. |
| 7,114,495 B2 | 10/2006 | Lockwood |
| 7,175,645 B1 | 2/2007 | Blach et al. |
| 2002/0000227 A1 | 1/2002 | Duyke et al. |
| 2003/0000521 A1 * | 1/2003 | Beaudry .................. 128/200.24 |
| 2005/0247317 A1 * | 11/2005 | Lockwood, Jr. ......... 128/206.11 |
| 2008/0097517 A1 * | 4/2008 | Holmes et al. ................ 606/199 |
| 2010/0298861 A1 * | 11/2010 | Fenton .......................... 606/199 |

FOREIGN PATENT DOCUMENTS

ES  289561  10/1995

* cited by examiner

SECTION AA

SECTION BB

NASAL DILATOR WITH CUSHION LAYER AND VARIABLE SPRING RATE

BACKGROUND OF THE INVENTION

This invention relates to an improvement to the configuration of nasal dilators such as those described in Spanish Patent No. 289,561 to Iriarti dated 15 Sep. 1986 and in the further patents discussed below. Generally speaking these dilators employ a resilient band which has an adhesive on the bottom side and sufficient length so that the resilient band can be bent over the bridge of the nose, and each end of the band becomes adhesively attached to the soft tissue on the lateral wall of the nasal passage.

Bending the resilient band from its initial planar state to its deformed state with its ends in contact with the lateral walls of the nasal passages and the center of the band overlying the bridge of the nose results in forces tending to pull out on the lateral wall tissues which stabilize the walls of the nasal passages during breathing.

The present invention improves nasal dilators by providing them with a resilient member which has a variable spring rate that decreases from the point where the resilient band crosses the bridge of the nose to the point where the resilient band terminates at the lateral wall of the nasal passage.

The nasal dilator of the present invention has a soft fabric cushion of the same or a slightly greater thickness than the resilient member. The soft fabric cushion is located in the same layer as the resilient member and covers the area of the soft fabric cover which is not in direct contact with the resilient member. The soft fabric cushion is in contact with edges of the resilient member and prevents the edges of the resilient member from pressing into the skin on the user's nose while using the nasal dilator.

The present invention further provides a convex protrusion on the side of the dilator at the center of the bridge of the nose facing the tip of the nose to indicate to the user the proper orientation of the dilator when applying it to the nose.

Blockage of the nasal passages from swelling due to allergies, colds and physical deformities can lead to breathing difficulty and discomfort. The nasal passages have mucus membranes which condition the air in the nasal passages prior to its arrival in the lungs. If the nasal passages are constricted due to swelling or minor deformities then the alternative is to breathe through the mouth. This means that the air bypasses the mucus membranes, losing the conditioning effects and causing irritation in the throat and lungs. At night, restrictions to breathing through the nasal passages can lead to snoring and/or sleep disturbances. In some cases, the restricted air supply can cause sleep problems brought on by a lack of oxygen.

For people with chronic blockages in the nasal passages, the alternative to correct the problem has been expensive surgery or medication. People with minor deformities and breathing problems brought on by swelling of the walls of the nasal passageways have been turning to various products fitted in or on the nose which claim to open the nasal passages.

The structure of the nose limits the options available for the design of nasal dilators. The nose terminates at the nostril, which has a slightly expanded volume immediately above it known as the vestibule. Above the vestibule, the nasal passage becomes restricted at a point called the nasal valve. At the nasal valve, the external wall of the nose consists of soft skin known as the lateral wall, which will deform with air pressure changes induced within the nasal passage during the breathing cycles. Above the nasal valve the nasal passage opens up to a cavity with turbinates over the top of the palate and turns downward to join the passage from the mouth to the throat.

The external structure of the nose consists of a skin covering over the nasal bones which are part of the skull. This gives the top of the nose a rigid structure at its base. Beyond the rigid nose bones, there is thin cartilage under the skin which is attached to the septum, which in turn contributes to the outside shape of the nose. The septum forms the wall between the two nostrils and may, if it is crooked, contribute to breathing problems.

As an alternative to surgery, the structure of the nose and the current art leave two main alternatives for the design of nasal dilators. One alternative uses a tube or a similar structure which can be inserted into the nasal passage to hold it in the open position allowing the free passage of air. The disadvantage to this design is that the dilator structure covers up the mucus membranes which condition the air. Also dilators of this design are uncomfortable and can irritate the walls of the nasal passage.

Another alternative is a dilator design, taught by the Iriarti patent for example, where each end that attaches to the external lateral wall of each of the nasal passages has resilient means connecting the ends for developing an external pulling force on the lateral wall causing it to open the nasal passage. This design has the advantage over the first alternative because the nasal passages are not disturbed by an internal insert. This design has limited control over the resilient force on the lateral wall of each of the nasal passages, and the resilient members crossing over the bridge of the nose can cause discomfort.

The present invention is an improvement over earlier nasal dilator configurations because it redistributes the lifting forces within the resilient band by modifying the spring rate, so that they can provide optimum lift on the lateral walls of the nasal passage. In addition maximum comfort for the user is achieved by adding the cushion layer at the same level as the resilient member to prevent the edge of the resilient member from pressing into the skin on the user's nose.

There is prior art which permits for adjusting the spring rate of the resilient band in the nasal dilator. For example, U.S. Pat. No. 5,476,091 to Johnson employs two parallel resilient bands of constant width and constant thickness which cross over the bridge of the nose and terminate at the outer wall of each nasal passage. The Johnson patent shows a plurality of notches cut into the top of each end of the resilient band to reduce the spring rate, which in turn prevents the end of the resilient band from peeling away from the skin. Each notch is a single point reduction of the spring rate with the spring rate reduction determined by the depth of the notch.

U.S. Pat. No. 5,479,944 to Petruson and U.S. Reissue Pat. No. Re 35,408 to Petruson provide nasal dilators with a one-piece molded plastic strip, the ends of which carry tabs for insertion into the nostrils.

U.S. Pat. No. 5,611,333 to Johnson shows the same concept of single point reduction in the spring rate of the resilient band using the notches shown in U.S. Pat. No. 5,476,091 mentioned above. In addition, the '333 Johnson patent shows other designs for the resilient band with either holes or slots which are located at the ends of the resilient bands and are intended to reduce the spring rate at a single point to prevent the end of the resilient band from peeling away from the skin.

U.S. Pat. No. 6,029,658 to Voss shows a beam-shaped resilient band which extends from one side of the user's nose across the bridge of the nose to the other side of the nose. The resilient band is made of plastic and has a varying thickness and width over the entire span. The resilient band exhibits a rigidity increase from the center towards the two respective ends which attach to the sides of the user's nose, which is the exact opposite of what is attained with the present invention.

U.S. Pat. No. 6,453,901 to Ierulli discloses several nasal strip configurations where the cover member extends beyond the perimeter of the spring member, including one embodiment in which the strip has some degree of variation in the spring force over a portion of the length of the strip.

Some of the better known nasal dilator patents, such as U.S. Pat. No. 5,533,499 to Johnson, U.S. Pat. No. 5,533,503 to Doubrek et al., and U.S. Pat. No. 6,318,362 to Johnson, all teach of nasal dilators with a cushion layer between the resilient member and the user's skin. U.S. Pat. No. 6,058,931 to Muchin is similar to the Spanish Iriarti patent in that the resilient member is in direct contact with the user's skin and no cushion layer is provided. These nasal dilators differ from the current invention, which provides a cushion layer at the same level in the nasal dilator structure which prevents the edge of the resilient member from pressing into the user's skin, but at the same time does not prevent contact of the resilient member from the user's skin.

Even the most recent nasal dilator patents such as U.S. Pat. No. 6,694,970 to Spinelli, U.S. Pat. No. 6,769,428 to Cronk et al., and U.S. Pat. No. 6,769,429 to Benetti do not have the resilient member with a constantly varying spring rate which is diminishing from the centerline to each end of the resilient member in combination with the cushion layer located at the same level as the resilient member. U.S. Pat. No. 7,114,495 to Lockwood does have the resilient member with a constantly varying spring rate which diminishes from the centerline to each end of the resilient member. However, it has a cushion layer under the resilient member. In contrast, the cushion layer of the nasal dilator of the present invention is at the same level as, and surrounds, the resilient member.

BRIEF SUMMARY OF THE INVENTION

An object of this invention is to provide a nasal dilator which exhibits improved performance relative to the nasal dilator known from the prior art.

An important feature of the present invention is to provide a soft fabric cushion layer which is the same size and shape as the top soft fabric cover and has adhesives on both sides. The cushion layer is at the same level as the resilient member and equal to or slightly thicker than the resilient member. As a result, the cushion layer and the resilient member are substantially flush where they meet. Since the resilient member is attached to the bottom of the top fabric cover by adhesives, the cushion layer surrounds the edge of the resilient member and covers the remaining area of the top soft fabric cover not covered by the resilient member. The adhesive on the bottom of the cushion layer is in contact with the skin on the user's nose when the dilator is in use.

Another improvement feature of the present invention is to configure the resilient band to reduce the width gradually from the center of the resilient band towards each end in a way that gradually reduces the spring rate of the resilient band. The thickness of the resilient band remains constant over its entire length, which simplifies the structure while keeping costs low.

A further improvement of the present invention is that the new dilator has a relatively greater width at its center with the shape of the bottom edge provided with a slight convex protrusion which points to the tip of the nose when the dilator is in use. The outer shape of the dilator is configured to optimize the location of the resilient member over the soft tissues on the outer wall of the nasal passages where the dilating forces are most effective.

Other improvements provided by the present invention are the four slits in the top soft fabric cover and the cushion layer at the boundary that separates the ends of the dilator from the intermediate structure which connects the ends of the dilator. The four slits are close to perpendicular to the longitudinal axis of the dilator and allow the top soft fabric cover and cushion layer to conform to the many different shapes of the outer walls of the nasal passages.

An additional improvement of the present invention is the use of transparent materials for the top soft fabric cover, the resilient member, and the cushion layer. Here too the cushion layer has a thickness that is equal to or slightly thicker than the resilient member. The normal color for the top soft fabric cover is tan; however, for sports applications the cover may be black or some other dark color.

The nasal dilator of the present invention is a significant unobvious improvement over the prior art. Nasal dilators that have been in the market for more than 10 years have a resilient member held in place on the user's nose by a top cover that defines the length and width of the dilator as well as adds additional adhesive surface to overcome the stresses developed by the resilient member. Another nasal strip that has been sold in the past has a resilient member sandwiched between a top surface which defines the length and width of the dilator and a cushion layer that covers the entire bottom surface of the top layer. Both of these dilators use current converting technology in their manufacturing process.

The improved nasal dilator of the present invention uses a new converting technology that has not been available until now. The new converting process requires that the resilient member be formed and located on the bottom surface of the top cover in a precise location. At the same time the cushion layer must have an opening cut and be precisely indexed, so that the edges of the cushion layer match up to the respective edges of the resilient member in order to achieve the contiguous bottom surface required by the improved dilator. This improvement in precision in the converting process is due to computer-controlled indexing, as well as a special webbing, which do not form part of the present application.

The improvements summarized above enhance the performance of the dilator and make the dilator more comfortable for the user as compared to prior art dilators in general and the Iriarti dilator in particular.

BRIEF DESCRIPTION OF THE DRAWINGS

The unique advantages of the present invention will become apparent to one skilled in the art upon reading the following specification and by reference to the following drawings.

DETAILED DESCRIPTION OF THE INVENTION

Figure 1:
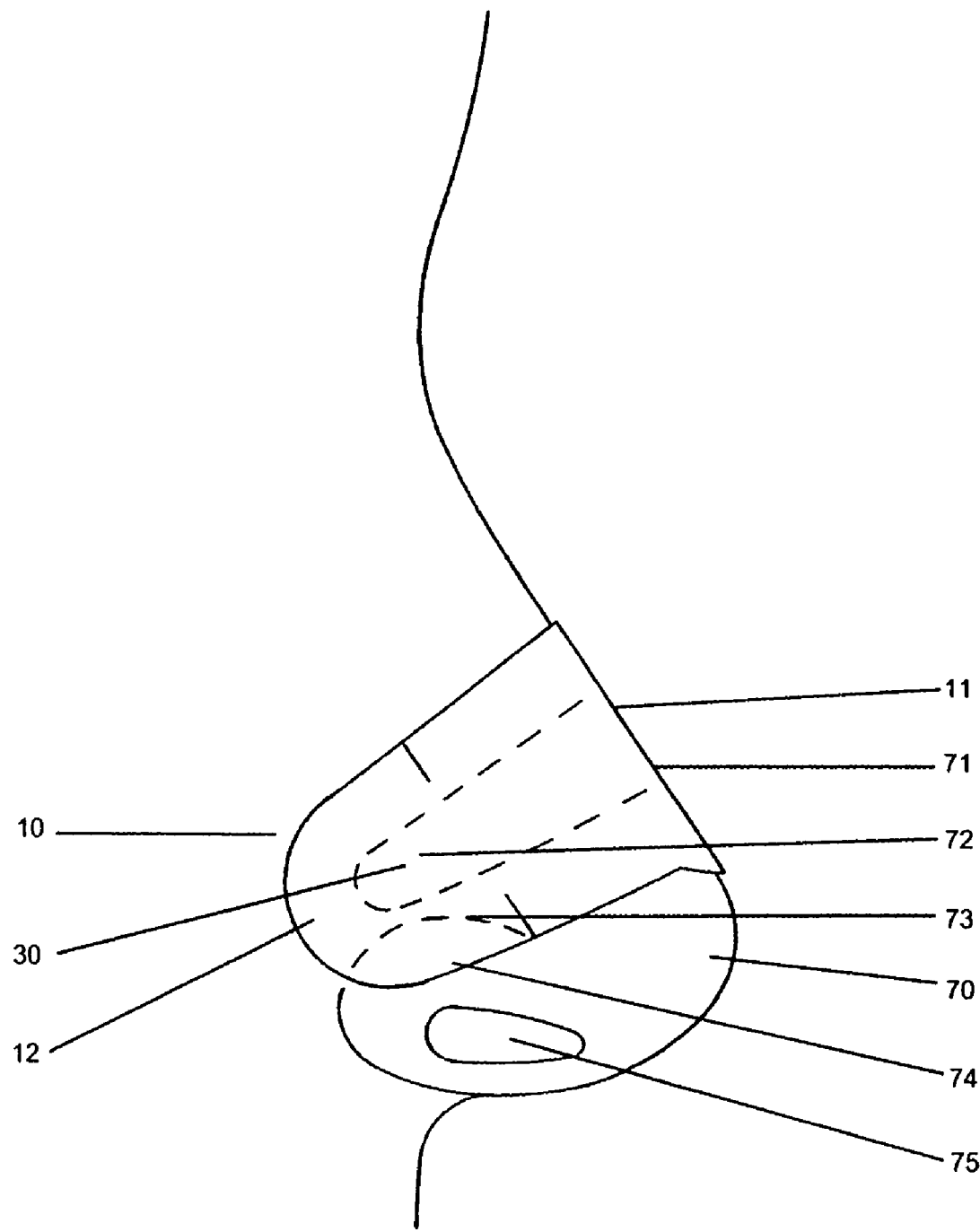
FIG. 1 is a side view of the dilator on the nose.

The specific improvements provided by this invention over past nasal dilators described in the prior art are best seen in the attached drawings.

Referring to FIGS. 1-4, the new nasal dilator 10 is mounted on the nose 70 of the user. The nasal dilator 10 has a center 11 that is bent over the bridge 71 of the nose 70, and each end 12 and 13 of the nasal dilator 10 is positioned over the lateral wall 72 of the nose 70.

The lateral wall 72 of the nasal passage 75 is located in the soft tissue 73 above the nostril flare 74, which in turn is adjacent to the entrance of the nasal passage 75. When the nasal dilator 10 which contains a resilient band 30 is deformed from its normally planar state by being bent over the bridge 71 of the nose 70, the ends 12 and 13 which are attached to the lateral wall 72 of the nasal passage 75 tend to pull on the lateral wall 72 in a way that opens the nasal passage 75 and improves the air flow through the nasal passages 75 during breathing. This invention shows improvements to the performance of the nasal dilator 10, makes the nasal dilator 10 easier to use, and increases the comfort of the nasal dilator 10 when it is used to dilate the lateral walls 72 of the nasal passages 75.

The new nasal dilator of the present invention has a top cover 20 which establishes the length and width of the nasal dilator 10, a resilient member 30 which is attached to the bottom surface 22 of the top cover 20, and a cushion layer 40 which is equal in thickness to the resilient member 30 and covers all of the bottom surface 22 of the top cover 20 that is not in contact with the top surface 38 of the resilient member 30. The dilator is flat in its natural state with the thickness of the nasal dilator 10 that is constant over the entire surface of the top cover 20 including surfaces in contact with the resilient member 30 and the cushion layer 40. The cushion layer 40 has an adhesive 43 which is in contact with the skin on the user's nose 70 when the nasal dilator 10 is in use. The bottom surface 37 of the resilient member 30 does not have an adhesive which is in contact with the skin on the user's nose 70. The top cover 20 does not contact the skin on the user's nose 70 when the nasal dilator 10 is in place, which is a unique feature of the nasal dilator of the present invention.

Figure 2:
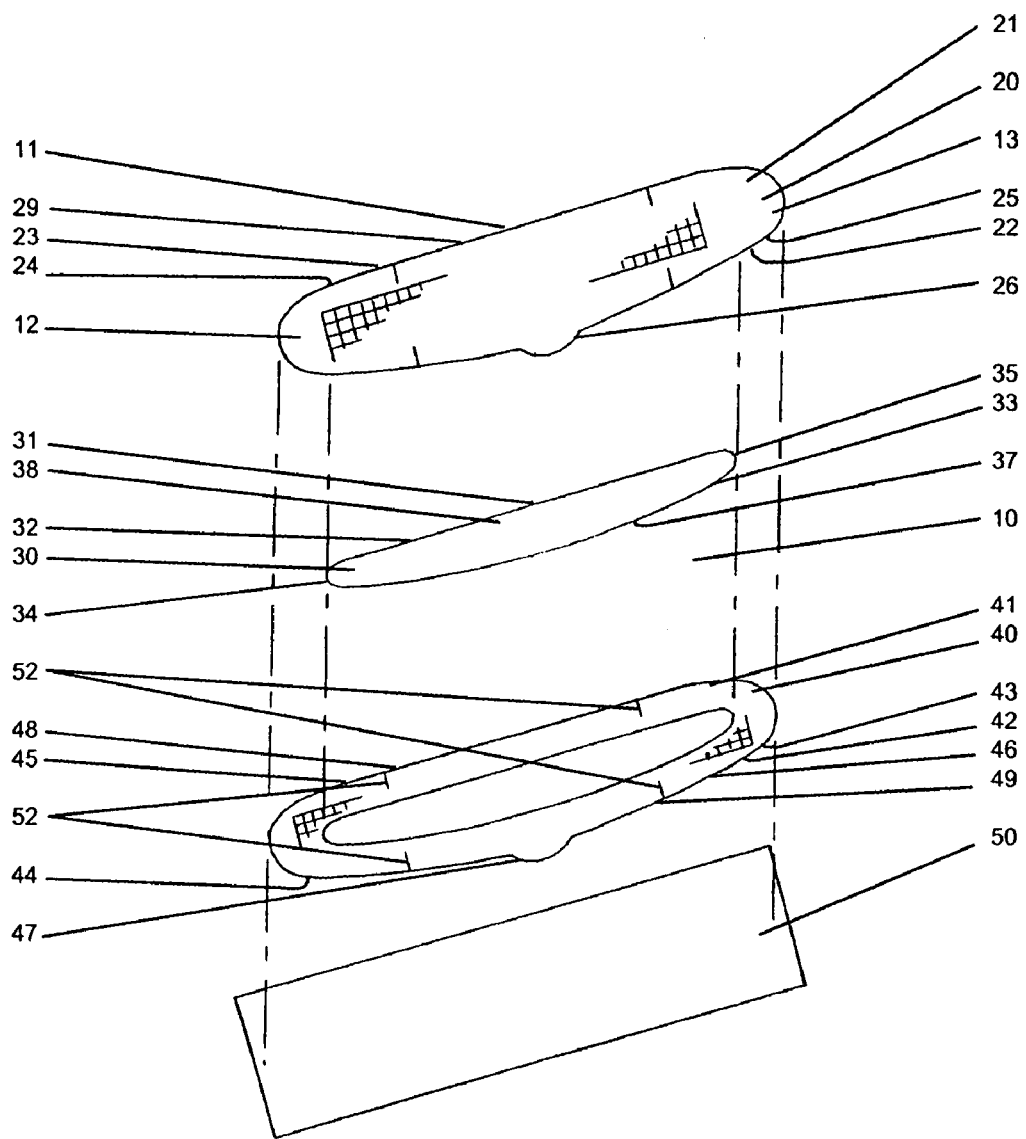
FIG. 2 is an exploded perspective top view of the components making up the dilator.

As is best seen in FIG. 2, the nasal dilator 10 is made up of several layers. The first layer is the top cover 20 which is made from a non-woven polyester cellulose fabric or equal which is usually tan in color on the top surface 21. The top surface 21 of the top cover 20 can be dyed in any color or imprinted with a brand, logo or other information. The top cover 20 also has a bottom surface 22 which is coated with a 3 mils acrylic hypoallergenic medical grade pressure-sensitive type adhesive 25 or equal. The adhesive 25 covers the entire bottom surface 22 of the top cover 20.

The top cover 20 has two sides 23 and 24 which run over the length of the top cover 20 with the exception of an approximately 0.5-inch wide section at the center 11 of the nasal dilator 10. On one side 23 of the top cover 20, there is a convex protrusion 26 which is configured to indicate the proper orientation of the nasal dilator 10 when it is in use. When the nasal dilator 10 is properly positioned on the user's nose, the convex protrusion 26 at the center 11 of the nasal dilator 10 is pointed towards the tip of the user's nose 70.

The second layer is the resilient member, 30, a plastic layer, which is made from a polyester sheet which is about 0.010 inch to about 0.015 inch thick, depending on the required strength of the nasal dilator 10. The thickness selected of the resilient member 30 is constant over the entire length of the resilient member 30, and the width of the resilient member 30 is greatest at the center 31 where the nasal dilator 10 passes over the bridge of the nose 71. The bottom edge 33 of the resilient member 30 curves toward the top edge 32 as the distance from the center 31 of the resilient member 30 is increased. This reduction of the width of the resilient member 30 causes a reduction of the spring rate in the resilient member 30 over the span from the center 31 to each of the ends 34 and 35 of the resilient member 30. The width at the center 31 of the resilient member 30 is less than half of the width of the top cover 20, and the width of the resilient member 30 at each of the ends 34 and 35 is approximately half of the width of the center 31.

The bottom edge 33 of the resilient member 30 between the center 31 and the respective ends 34 and 35 is curved over the length of the strip and is asymmetrical in relation to the longitudinal center line 36 (see FIG. 3) of the resilient member 30. Other curves for edges 32 and 33 are possible as long as the maximum width of the resilient member 30 is at the center 31 and the spring rate is reduced as the distance from the center 31 is increased until reaching ends 34 and 35. To attain the desired force distribution and to prevent the development of torsional forces, the radius of curvature of the edges 32 and 33 of the resilient member 30 is greater than 1.5 inches. In addition, the thickness of the resilient member 30 is 3% or greater than the width of the resilient member 30 at the longitudinal center line 36 in order to establish a baseline spring rate at the centerline of the resilient member 30 and allow for the reduction of width of the resilient member 30 over the span to the ends 34 and 35 in which the polyester of specified thickness will achieve a lifting force of 25 to 30 grams. This ratio increases as the distance from the center 31 is increased, and the width of the resilient band decreases until reaching ends 34 and 35.

In the same layer as the resilient member 30, there is a cushion layer 40 which is equal to or slightly thicker than the resilient member 30 and surrounds the edges 32 and 33 of the resilient member 30. In this embodiment the edges 48 and 49 of the cushion layer 40 that are adjacent to the respective edges 32 and 33 of the resilient member 30 have the same curvature as the resilient member 30 in order to form a contiguous surface between the bottom 42 of the cushion layer 40 and the bottom 37 of the resilient member 30. This will prevent the edge of the resilient member 30 from pressing into the user's skin while the nasal dilator 10 is in use.

The cushion layer 40 is made from non-woven polyester cellulose fabric which is about 0.010 inch to about 0.015 inch thick. The cushion layer 40 is attached to the bottom surface 22 of the top cover 20 which is not covered by the resilient member 30. As a result, the bottom 37 of the resilient member 30 and the bottom 42 of the cushion layer 40 are in contact with the skin on the user's nose 70, while the top cover 20 cannot come in contact with the user's nose 70 when the nasal dilator 10 is in use. This also distinguishes this present invention from the prior art because all known nasal dilators either have a cushion layer 40 that prevents the resilient member 30 from contacting the skin on the user's nose 70 or have no cushion layer 40 which allows both the bottom surface 22 of the top cover 20 and the bottom surface 37 of the resilient member 30 to have direct contact with the skin on the user's nose 70.

The bottom 42 of the cushion layer 40 is coated with a 3 mils acrylic hypoallergenic medical grade pressure-sensitive type adhesive 43 or equal that is designed to hold the nasal dilator in place on the user's nose 70. The adhesive 43 on the bottom 42 of the cushion layer 40 has sufficient strength when adhering to the user's nose 70 to overcome the stresses developed by the resilient member 30 when the resilient member 30 is deformed to conform to the surface of the skin of the user's nose 70. The cushion layer 40 has two sides 45 and 46 which match the two respective sides 23 and 24 of the top cover 20. The cushion layer 40 also has a convex protrusion 47 which matches the convex protrusion 26 of the top cover 20.

A release liner 50 is provided to protect the adhesive surface 43 on the bottom side of the cushion layer 40. This release liner 50 is removed from the nasal dilator 10 prior to applying the nasal dilator 10 to the skin of the user's nose 70.

Figure 3:
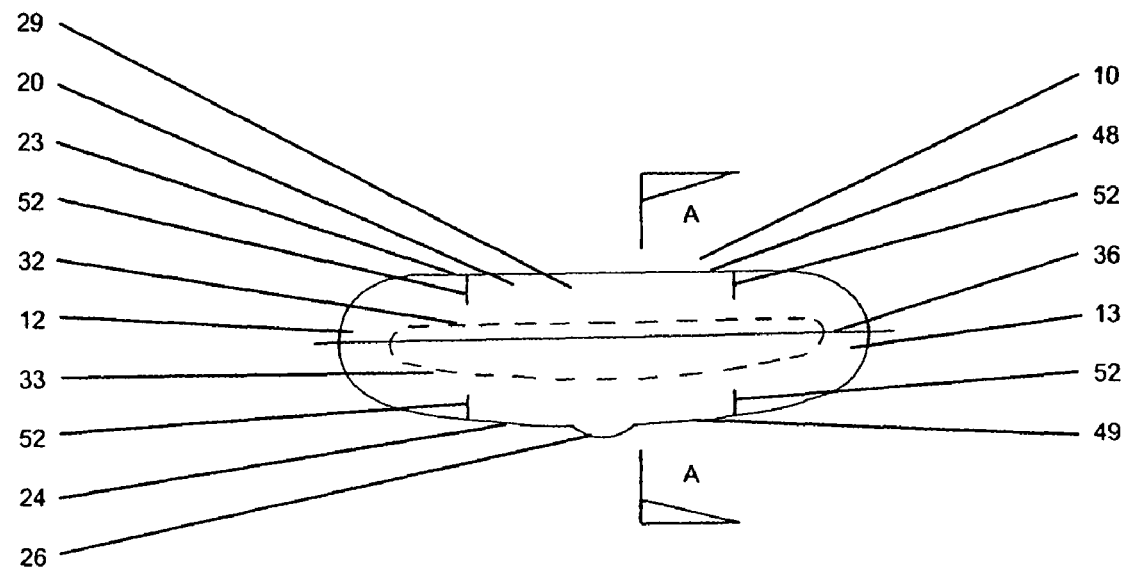
FIG. 3 is a top view of the dilator with a single resilient band.
Figure 4:
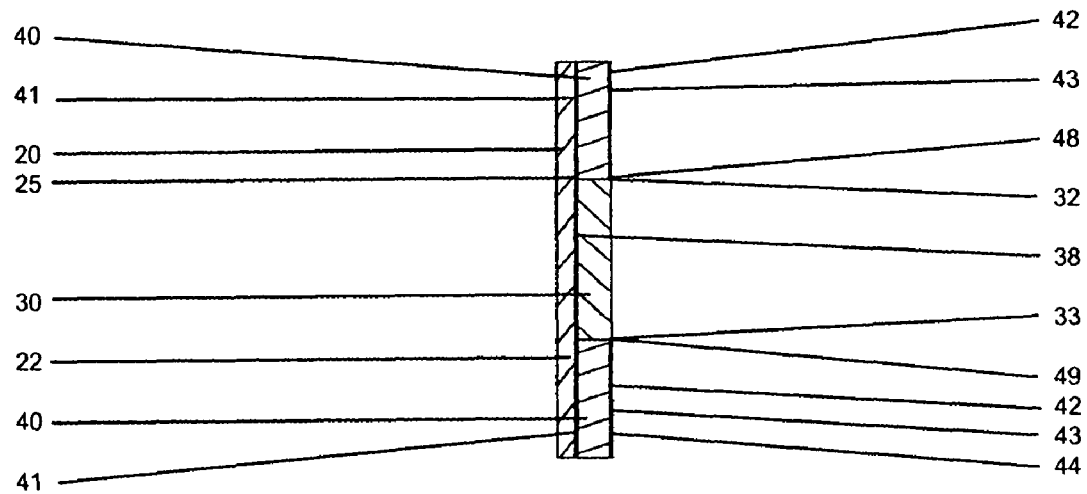
FIG. 4 is a sectional view of the dilator in FIG. 3 showing the layers of the components that make up the dilator.

FIGS. 3 and 4 show a top view of the first embodiment of the nasal dilator 10 and a cross-sectional view (AA) which is perpendicular to the longitudinal axis 36 of the nasal dilator 10. The cross-sectional view shows the top cover 20 with adhesive 25 on the bottom surface 22 which is in direct contact with the top surface 38 of the resilient member 30 and the top surface 41 of the cushion layer 40. The edges 32 and 33 of the resilient member 30 are in direct contact with the edges 48 and 49 of the cushion layer 40 forming a contiguous bottom surface 44 which prevents the edges 32 and 33 of the resilient member 30 from pressing into the skin on the nose 70 of the user when the nasal dilator 10 is in use.

Figure 5:
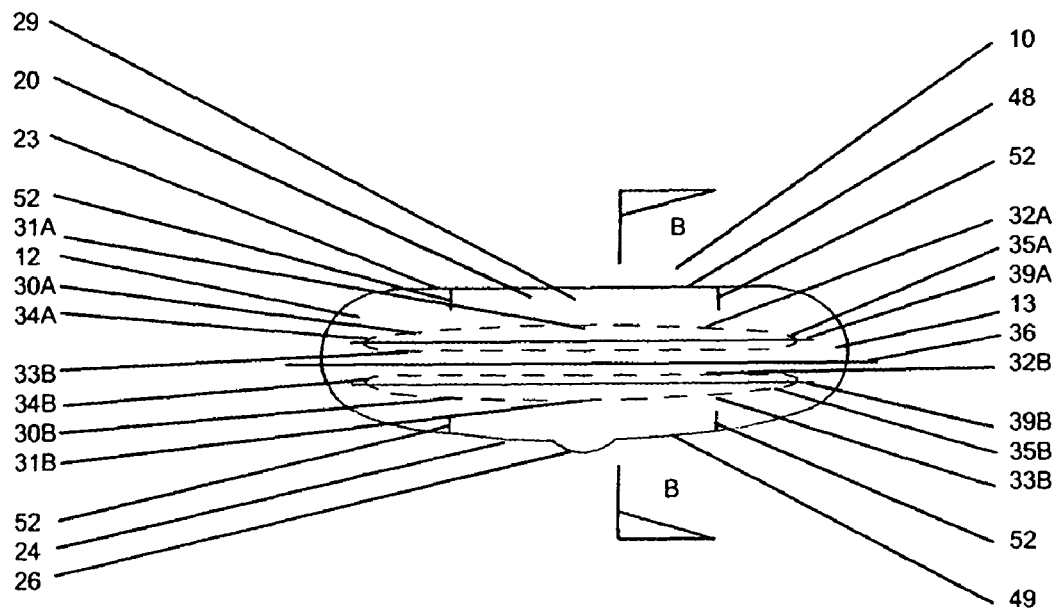
FIG. 5 is a top view of the dilator with two resilient bands.
Figure 6:
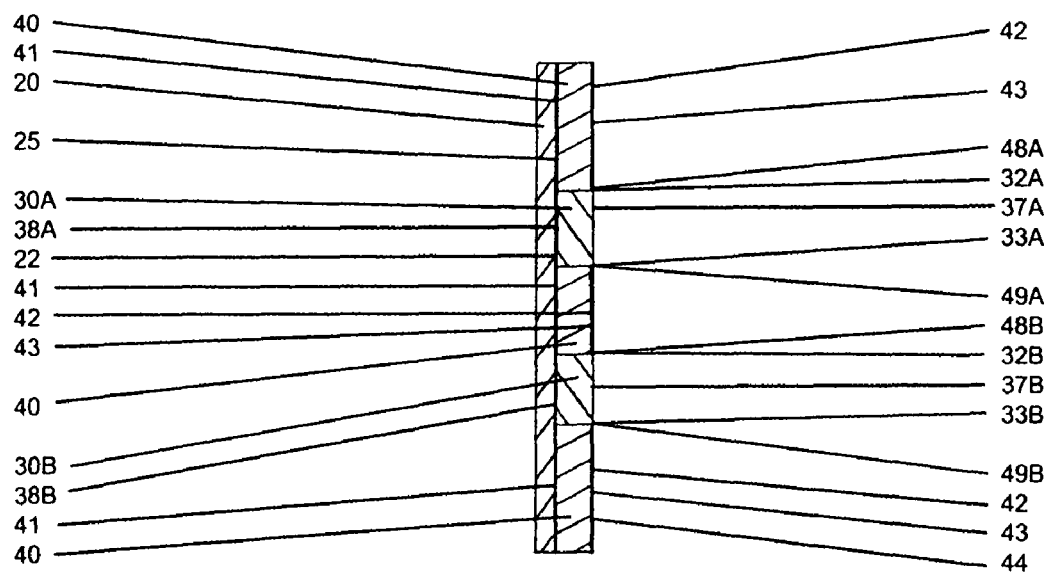
FIG. 6 is a sectional view of the dilator in FIG. 5 showing the layers of the components that make up the dilator.

FIGS. 5 and 6 show a top view of another embodiment of the nasal dilator 10 and its respective cross-sectional view (BB) which is perpendicular to the long axis of the nasal dilator 10. The edges 32 (A&B) and 33 (A&B) of two resilient members 30 (A&B) are shown. The cross-sectional view (BB) shows the top cover 20 with adhesive 25 on the bottom surface 22 which is in direct contact with the top surface 38 (A&B) of the resilient members 30 (A&B) and the top surface 41 of the cushion layer 40. The top cover 20 is made from non-woven polyester cellulose fabric or equal and the top cover 20 defines the length and width of the nasal dilator 10.

The second layer has two or more resilient members 30 (A&B) which are made from a polyester sheet which is about 0.010 inch to about 0.015 inch thick, depending on the required strength of the nasal dilator 10. The thickness selected of the resilient members 30 (A&B) is constant over the entire length of the resilient members 30 (A&B), so the nasal dilator 10 can be manufactured in a converting process. The width of the resilient members 30 (A&B) is constantly decreasing from the center 31 (A&B) of the resilient members 30 (A&B) to each end 34 (A&B) and 35 (A&B) in this particular embodiment, and the thickness of the resilient members 30 (A&B) is 3% or greater than the width of the resilient member over the length of the nasal dilator.

As can be seen in FIG. 6, the resilient members 30 (A&B) are attached to the bottom surface 22 of the top cover 20 with the adhesive 25 that is applied to the bottom surface 22 of the top cover 20. The resilient members 30 (A&B) are parallel to the longitudinal axis 36 of the top cover 20 with each of the ends 34 (A&B) and 35 (A&B) terminating short of the end edges of the top cover 20. The resilient members 30 (A&B) have no adhesive on the bottom surface which is in contact with the user's skin when the nasal dilator 10 is in use.

Each of the resilient members 30 (A&B) can be symmetrical or asymmetrical to the longitudinal axis 39 (A&B) of the resilient members 30 (A&B). Symmetry is achieved by using identical curves for sides 32 (A&B) and 33 (A&B) between the center 31 (A&B) and the ends 34 (A&B) and 35 (A&B) of the resilient members 30 (A&B). The concept of using a reduction of the width in the resilient members 30 (A&B) that causes a reduction of the spring rate in the resilient members 30 (A&B) can be used in nasal dilator 10 with one or more parallel resilient members 30 (A&B) that extend parallel to the longitudinal axis 36 of the nasal dilator 10.

In the same layer as the resilient members 30 (A&B), there is a cushion layer 40 which is equal to or slightly thicker than the resilient members 30 (A&B) and surrounds the edges 32 (A&B) and 33 (A&B) of the resilient members 30 (A&B).

The cushion layer 40 is designed to form a contiguous surface between the bottom 42 of the cushion layer 40 and the bottoms 37 (A&B) of the resilient members 30 (A&B) to prevent the edges 32 (A&B) and 33 (A&B) of the resilient members 30 (A&B) from pressing into the user's skin while the nasal dilator 10 is in use. The cushion layer 40 is made from non-woven polyester cellulose fabric which is about 0.010 inch to about 0.015 inch thick including the thickness of the attached adhesive 43. The cushion layer 40 is attached to the bottom surface 22 of the top cover 20 which is not covered by the resilient members 30 (A&B), and the edges 48 (A&B) and 49 (A&B) of the cushion layer 40 are in contact with the respective adjacent edges 32 (A&B) and 33 (A&B) of the resilient members 30 (A&B).

The bottom 42 of the cushion layer 40 is coated with a 3 mils acrylic hypoallergenic medical grade pressure-sensitive type adhesive 43 or equal capable of withstanding the stresses caused by the resilient members 30 (A&B) and holding the nasal dilator 10 in place on the user's nose 70. Depending on the specific converting process used to manufacture the nasal dilator 10, the cushion layer 40 may also have the same 3 mils acrylic adhesive on the top surface 41 to control any stretch in the fabric during manufacturing.

To protect the adhesive surface 43 on the bottom surface 42 of the cushion layer 40, a release liner 50 is provided as shown in FIG. 2. This release liner 50 is pealed away exposing the adhesive 43 on the bottom of the cushion layer 40 when the nasal dilator 10 is ready to be placed on the nose 70.

The nasal dilator 10 in both embodiments is normally in a planar state when it is removed from the release liner 50 and has no stresses. When the nasal dilator 10 is bent over the bridge 71 of the nose 70 and the ends 12 and 13 are engaged with the lateral wall 72 of the nasal passage, then the stresses introduced in the resilient member 30 cause the ends 12 and 13 of the nasal dilator 10 to pull outwardly and upwardly on the lateral wall 72 to improve the breathing of the user.

The nasal dilator 10 in both embodiments can also be provided as a clear nasal dilator 10. In this case, the top cover 20 is made from a 3 mil polyethylene with the bottom surface 22 coated with 2 mils acrylic hypoallergenic medical grade adhesive 25. The resilient member 30 in both embodiments is made from the clear polyester and the cushion layer 40 is made from 8 mil polyethylene with both the top surface 41 and the bottom surface 42 coated with 2 mils acrylic hypoallergenic medical grade adhesive 43.

Referring to FIGS. 1, 2, 3 and 5 there are four slits 52 in the top soft fabric cover 20 and the cushion layer 40 at the boundary of the ends 12 and 13 of the nasal dilator 10 and the intermediate structure 29 which connects the two ends 12 and 13. The four slits 52 are shown to be perpendicular to the longitudinal axis 36 of the nasal dilator 10, and they allow the top soft fabric cover 20 and the cushion layer 40 to conform to the many different shapes of the outer wall tissue 73 of the nasal passages 75. In some cases the slits 52 may be cut at an angle to the longitudinal axis 36 of the nasal dilator 10.

Figure 7:
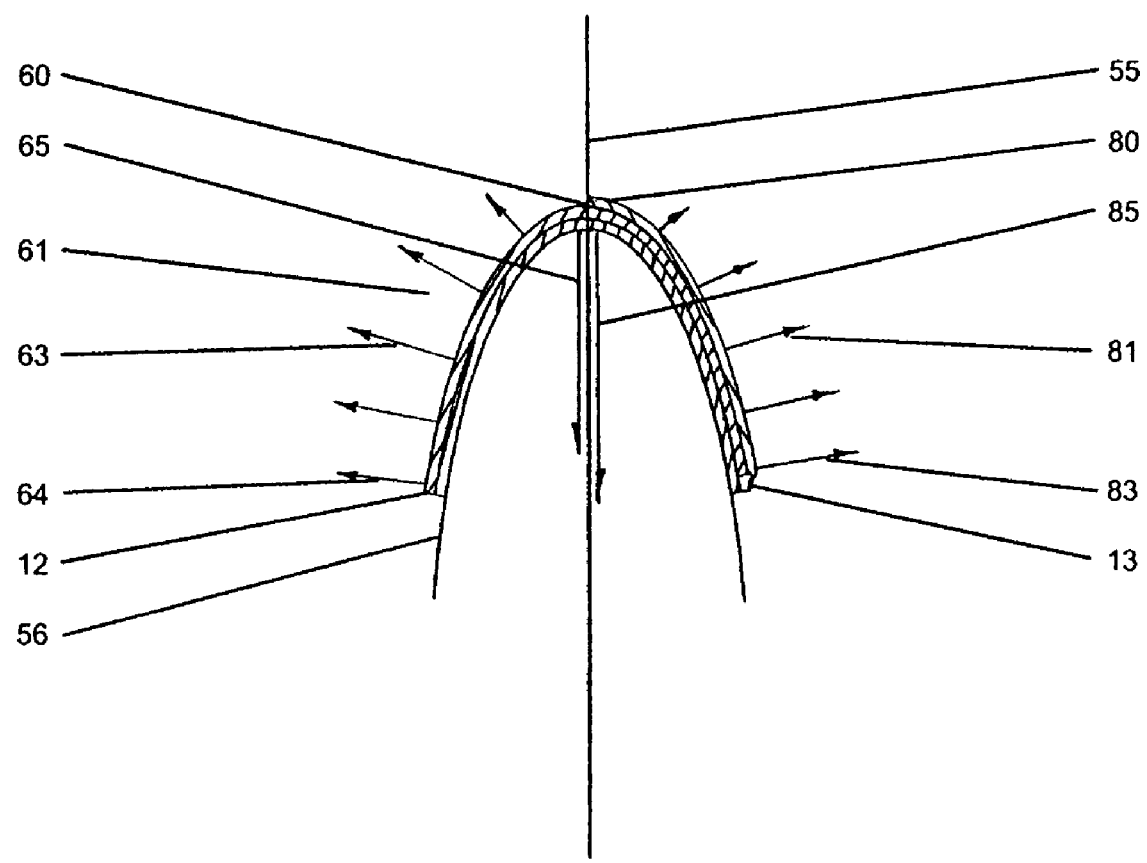
FIG. 7 is a drawing showing the force vectors of the dilator in this invention compared to the force vectors in other, known dilators.

The use of a resilient band 30 with a decreasing spring rate in a nasal dilator 10 has a positive effect on the nasal dilator 10 performance. FIG. 7 shows a comparison of the performance of a nasal dilator 10 with a decreasing spring rate 60 on the left side of the vertical centerline 55 and a nasal dilator with a constant spring rate 80 on the right side of the vertical centerline 55. The nasal dilator 10 is shown bent over an elliptical surface 56 which represents the skin 76 of the user's nose 70.

The nasal dilator 10 with the decreasing spring rate 60 has a series of vectors 61 pulling out on the elliptical surface 56. Vectors 61 which are further away from the vertical centerline 55 increase to vector 63. Then they begin to decrease to vector 64 at the end 12 of the nasal dilator 10. The vectors 61 on the side with the decreasing spring rate 60 cause the lateral wall 72 to be pulled up and out at the center of the nasal passage 75, which improves the air flow in the nasal passage 75. A reactive vector 65 provides an opposing force to vectors 61.

The right-hand side of FIG. 7 illustrates the forces generated by a nasal dilator 10 with a constant spring rate 80. It generates a series of vectors 81 pulling out on the elliptical surface 56. As the vectors 81 move away from the vertical centerline 55, they increase until the last vector 83. This means that the pull on the lateral wall 72 is outward and that the maximum vector 83 is pulling out on the lateral wall 72 at the edge of the nasal passage 75. Although air flow is improved, the nasal dilator 10 with the decreasing spring rate 60 provides better performance because it opens the lateral wall 72 adjacent to the center of the nasal passage 75 where the maximum air volume flows. Also the reactive vector 85 is greater than the reactive vector 65 for the decreasing spring rate 60 nasal dilator 10, which renders the constant spring rate 80 nasal dilator 10 less comfortable for the user.

The description of the preferred embodiment described herein is not intended to limit the scope of the invention, which is properly set out in the claims.

What is claimed is:

1. A nasal dilator capable of introducing separating stresses in nasal outer wall tissues, the dilator comprising:
    a top cover;
    a resilient member secured to the top cover and having a pair of spaced-apart end surfaces which, if forced toward one another from initial positions when the resilient member is flat to substantially reduce direct spacing therebetween by a spacing reducing force external to said resilient member, results in restoring forces in said resilient member tending to restore said direct spacing between said end surfaces;
    a cushion layer that has a thickness which is approximately equal to a thickness of the resilient member and has inner edges which are adjacent to outer edges of the resilient member, a bottom surface of both the cushion layer and the resilient member cooperating to form a contiguous surface; and
    engagement means adhered to said end surfaces and capable of engaging exposed surfaces of nasal outer wall tissues sufficiently to remain so engaged against said restoring forces.

2. A nasal dilator according to claim 1 wherein the resilient member is flat and a constantly diminishing spring rate is achieved by adjusting a width of the resilient member.

3. A nasal dilator according to claim 1 wherein the cushioning layer has adhesive on both sides to prevent direct contact of the top cover and the exposed surfaces of nasal outer wall tissues.

4. A nasal dilator according to claim 1 wherein the resilient member is asymmetrical to a long axis of the dilator.

5. A nasal dilator according to claim 1 wherein the resilient member is symmetrical to a long axis of the dilator.

6. A nasal dilator according to claim 1 including a set of slits on an outer edge of the top cover, each slit having lateral edges approximately perpendicular to a long axis of the top cover, each slit defining a boundary between an intermediate section and ends of the top cover.

7. A nasal dilator according to claim 1 including a convex protrusion on a bottom side of the dilator to facilitate a proper application of the dilator by a user thereof.

8. A nasal dilator according to claim 1 wherein the thickness of the dilator is constant over an entire surface of the top cover including an area laminated to the resilient member and the cushion layer.

9. A nasal dilator according to claim 1 wherein the top cover has longitudinal sides which are configured so that a width of the dilator is greatest at its center and diminishes towards each end.

10. A nasal dilator according to claim 1 wherein the top cover, the resilient member, and the cushion layer are fabricated of transparent materials.

11. A nasal dilator according to claim 1 wherein the top cover is colored.

12. A nasal dilator according to claim 1 wherein the top cover includes at least one of printing, a logo, and a visual design.

13. A nasal dilator according to claim 1 including a release liner protecting adhesive on the bottom surface of the cushion layer.

14. A nasal dilator according to claim 1 including at least two resilient members arranged side-by-side.

15. A nasal dilator according to claim 14 wherein the resilient members are parallel to each other.

16. A nasal dilator according to claim 14 wherein the resilient members are asymmetrical relative to its longitudinal centerline.

17. A normally planar nasal dilator for preventing outer wall tissue of nasal passages of a nose from drawing in during breathing, the dilator comprising:
    a top cover with a bottom surface and an adhesive on the bottom surface;
    a resilient member engaged with the bottom surface and having a constant thickness over its length and longitudinal sides which converge from a middle portion of the resilient member to respective ends of the resilient member; and
    a cushion layer which peripherally extends past an edge of the resilient member, and adhesively engages the bottom surface of the top cover, and surrounds the edges of the resilient member, a bottom surface of both the cushion layer and the resilient member cooperating to form a contiguous surface, and adhesive on the bottom surface of the cushion layer which engages the skin on the nose.

18. A nasal dilator according to claim 17 wherein the resilient member is flat and a constantly diminishing spring rate is achieved by adjusting the width of the resilient member.

19. A nasal dilator according to claim 17 wherein the cushioning layer has adhesive on both sides to prevent direct contact of the top cover and the skin on the nose.

20. A nasal dilator according to claim 17 including a release liner protecting adhesive on the bottom surface of the cushion layer.

21. A nasal dilator according to claim 17 wherein a thickness of the dilator is constant over an entire surface of the top cover including an area laminated to the resilient member and the cushion layer.

22. A nasal dilator for preventing outer wall tissue of nasal passages of a nose from drawing in during breathing, the dilator having a longitudinal axis, opposing ends, a centerline midway between the ends which is perpendicular to the longitudinal axis, and a normally substantially planar state, the dilator comprising:
    a top cover which has an adhesive on a bottom surface thereof;
    an elongated resilient member engaged with the bottom surface, extending in a longitudinal direction of the dilator, and having a constant thickness and sides which converge from a center of the resilient member to respective ends thereof;

a cushion layer that has a thickness which is approximately equal to the thickness of the resilient member and has edges which are adjacent to edges of the resilient member, a bottom surface of both the cushion layer and the resilient member cooperating to form a contiguous surface, and an adhesive on the bottom surface of the cushion layer for engaging skin tissue on the nose to secure the dilator to the nose.

23. A nasal dilator for preventing outer wall tissue of nasal passages of a nose from drawing in during breathing, the dilator having a longitudinal axis, opposing ends, a centerline midway between the ends which is perpendicular to the longitudinal axis, and a normally substantially planar state, the dilator comprising:

a top cover which has an adhesive on a bottom surface thereof;

an elongated resilient member engaged with the bottom surface, extending in a longitudinal direction of the dilator, and having a constant thickness and sides which converge from a center of the resilient member to respective ends thereof;

a cushion layer that has a thickness which is approximately equal to the thickness of the resilient member and has edges which are adjacent to edges of the resilient member, a bottom surface of both the cushion layer and the resilient member form a contiguous surface, and including an adhesive on the bottom surface of the cushion layer for engaging skin tissue on the nose to secure the dilator to the nose; and a set of slits in an outer edge of the dilator, the slits having lateral edges extending approximately perpendicular to the longitudinal axis of the dilator, each slit defining a boundary between an intermediate section and the ends of the dilator.

24. A nasal dilator according to claim 23 wherein the dilator has longitudinal sides which are configured so that a width of the dilator is greatest at its center and diminishes towards each end.

25. A nasal dilator according to claim 23 including a convex protrusion on a bottom side of the dilator to facilitate proper application of the dilator by the user.

26. A nasal dilator according to claim 23 wherein a thickness of the dilator is constant over an entire surface of the top cover including an area laminated to the resilient member and the cushion layer.

27. A nasal dilator according to claim 23 wherein the top cover, the resilient member, and the cushion layer are fabricated from transparent plastic materials.

28. A nasal dilator capable of introducing separating stresses in nasal outer wall tissue, the dilator comprising:

a plurality of elongated resilient members each forming a long axis and defining spaced-apart ends which, when forced toward one another from an initial, relaxed position of the resilient member to substantially reduce direct spacing between the ends by a force external to said resilient member, generate restoring forces in the resilient member tending to return the resilient member to its initial relaxed position;

at least one of the resilient members having a constant thickness over its length and sides generally extending in the direction of the long axis which converge from a center of the resilient members to the ends thereof so that the plurality of resilient members collectively has a spring rate which continuously diminishes from the center to said ends;

a cushion layer that has a thickness which is approximately equal to the thickness of the resilient members and has edges which are adjacent to the sides of the resilient members, a bottom surface of both the cushion layer and of the resilient members cooperating to form a substantially contiguous surface, and an adhesive on the bottom surface of the cushion layer for engaging skin tissue on a nose sufficiently to remain engaged while the restoring forces are active.

29. A nasal dilator according to claim 28 wherein the resilient members are flat and the constantly diminishing spring rate is achieved by adjusting a width of the resilient members.

30. A nasal dilator according to claim 28 including a top cover, wherein the cushioning layer has adhesive on both sides to prevent direct contact of the top cover and the skin tissue on the nose.

31. A nasal dilator according to claim 28 wherein the resilient members are asymmetrical to the long axis formed by the resilient members.

32. A nasal dilator according to claim 28 wherein the resilient members are symmetrical to the long axis formed by the resilient members.

33. A nasal dilator according to claim 28 wherein the resilient members are parallel to each other.

34. A nasal dilator according to claim 28 wherein the resilient members are asymmetrical relative to a longitudinal centerline.

35. A nasal dilator according to claim 28 including a set of slits on an outer edge of the at least one of the resilient members, each slit having lateral edges extending approximately perpendicular to the long axis, each slit defining a boundary between an intermediate section and the ends.

36. A nasal dilator according to claim 28 including a convex protrusion on a bottom side of the dilator to facilitate proper application of the dilator by a user.

37. A nasal dilator according to claim 28 including a top cover, wherein a thickness of the dilator is constant over an entire surface of the top cover including an area laminated to the resilient members and the cushion layer.

38. A nasal dilator according to claim 28 wherein the resilient members are arranged side-by-side and are configured so that a width of the side-by-side resilient members is greatest at its center and diminishes towards each end.

39. A nasal dilator according to claim 28 including a top cover, wherein the top cover, the resilient members, and the cushion layer are fabricated from transparent plastic materials.

40. A nasal dilator according to claim 28 including a release liner protecting the adhesive on the bottom surface of the cushion layer.

* * * * *